United States Patent
Tatawati

(10) Patent No.: US 12,409,114 B2
(45) Date of Patent: Sep. 9, 2025

(54) CLEANSING/SANITIZER COMPOSITIONS, METHODS AND APPLICATIONS THEREOF

(71) Applicant: Shivanand Tatawati, Belgaum (IN)

(72) Inventor: Shivanand Tatawati, Belgaum (IN)

(73) Assignee: TATWATI PHARMACEUTICALS PRIVATE LIMITED, Belgaum (IN)

( * ) Notice: Subject to any disclaimer, the term of this patent is extended or adjusted under 35 U.S.C. 154(b) by 852 days.

(21) Appl. No.: 17/604,440

(22) PCT Filed: Apr. 20, 2020

(86) PCT No.: PCT/IB2020/053720
§ 371 (c)(1),
(2) Date: Oct. 18, 2021

(87) PCT Pub. No.: WO2020/212958
PCT Pub. Date: Oct. 22, 2020

(65) Prior Publication Data
US 2022/0211592 A1    Jul. 7, 2022

(30) Foreign Application Priority Data

Apr. 18, 2019 (IN) .............. 201841039600

(51) Int. Cl.
*A61K 8/26* (2006.01)
*A61K 8/34* (2006.01)
*A61K 8/44* (2006.01)
*A61K 8/46* (2006.01)
*A61K 8/60* (2006.01)
*A61K 8/73* (2006.01)
*A61K 8/81* (2006.01)
*A61K 8/92* (2006.01)
*A61Q 19/10* (2006.01)

(52) U.S. Cl.
CPC .............. *A61K 8/26* (2013.01); *A61K 8/345* (2013.01); *A61K 8/44* (2013.01); *A61K 8/442* (2013.01); *A61K 8/466* (2013.01); *A61K 8/602* (2013.01); *A61K 8/732* (2013.01); *A61K 8/8176* (2013.01); *A61K 8/922* (2013.01); *A61Q 19/10* (2013.01); *A61K 2800/596* (2013.01)

(58) Field of Classification Search
CPC . A61K 8/26; A61K 8/345; A61K 8/44; A61K 8/442; A61K 8/466; A61K 8/602; A61K 8/732; A61K 8/8176; A61K 8/922; A61K 2800/596; A61Q 19/10
See application file for complete search history.

(56) References Cited

U.S. PATENT DOCUMENTS

2017/0096418 A1 *  4/2017  Patron ................. B65D 81/18

FOREIGN PATENT DOCUMENTS

| FR | 3042114 A1 | 4/2017 |
| WO | WO 2012075455 A2 | 6/2012 |
| WO | WO 2014135650 A1 | 9/2014 |
| WO | WO 2014158472 A1 | 10/2014 |

OTHER PUBLICATIONS

Translation of FR-3042114-A1. Belle, R. (Year: 2017).*
Ashland. Polyplasdone XL 10 Crospovidone. https://www.ashland.com/industries/pharmaceutical/oral-solid-dose/polyplasdone-xl10-crospovidone (Year: 2024).*
International Search Report mailed on Aug. 3, 2020, in the PCT Application No. PCT/IB2020/053720.
Written Opinion mailed on Aug. 3, 2020, in the PCT Application No. PCT/IB2020/053720.

* cited by examiner

*Primary Examiner* — Jennifer A Berrios
*Assistant Examiner* — Chasity P Janosko
(74) *Attorney, Agent, or Firm* — Trupti P. Joshi

(57) ABSTRACT

The present disclosure relates to the field of cleansing/sanitization, cosmetic technology, chemical and general sciences. In particular, the disclosure relates to saponification free cleansing compositions comprising at least one cleansing agent optionally along with adsorbing agent, excipient or a combination thereof. The disclosure also provides process of preparing said composition and its applications for cleansing/sanitizing skin and/or inanimate objects amongst others.

3 Claims, No Drawings

CLEANSING/SANITIZER COMPOSITIONS, METHODS AND APPLICATIONS THEREOF

CROSS-REFERENCE TO RELATED APPLICATIONS

The present application is a § 371 National Phase entry of International Application No. PCT/IB2020/053720, filed Apr. 20, 2020, which claims priority to Indian Patent Application number 201841039600, filed Apr. 18, 2019.

TECHNICAL FIELD

The present disclosure relates to the field of cleansing/sanitization, cosmetic technology, chemical and general sciences. In particular, the disclosure relates to saponification free solid cleansing compositions comprising at least one cleansing agent optionally along with adsorbing agent, excipient or a combination thereof. Preferably, the present saponification free solid cleansing compositions comprise a cleansing agent and excipient optionally along with adsorbing agent; wherein the cleansing agent is one or more surfactant and the excipient comprises at least one or more deodorizing agent or antimicrobial agent. The disclosure also provides process of preparing said compositions and its applications for cleansing the skin and/or inanimate objects.

BACKGROUND OF THE DISCLOSURE

At present, during development of products in the field of cosmetic technology and health hygiene, a lot of emphasis is being focused on improving mildness, physical characteristics, foam, conditioning effects and other properties including aesthetic aspects of personal cleansing compositions comprising soap. However, chemicals used in the saponification process can cause health hazards. Further, soaps made by saponification process require sophisticated plant running on a technology intensive operation and cause environmental pollution. Also, the existing soap-based formulations available mainly as multi time application products such as bars are very much prone to usage by more than one person. This may cause discouragement on the part of user since these products are meant for personal hygiene. Further, commercially available liquid based cleansing compositions are packaged in the form of a dispenser which can be used by many people and is thereby better from personal hygiene point of view when compared to the bars. However, personal hygiene conscious people may still hesitate to use them or rather, share them with multiple people. Further, multi time application products such as bars and liquid based products coming in dispensers are expensive. Furthermore, said formulations are susceptible to wastage due to spillage. In view of the above said limitations, soap bars and liquid soap based products receive low level of consumer acceptance particularly in geriatric and paediatric populations. Also, these formulations and widely available products such as liquid hand wash are expensive and not highly convenient to carry during travel. Additionally, there are additional limitations in the field of general public health such as unavailability of economical/low cost, efficient and handy cleansing products (especially for rural population) which are immensely useful during public health emergency/crisis (eg. epidemic/pandemic); unavailability of soap in most of the restaurants, public toilets, railways, schools; presence of unhygienic, harmful and low cost soaps; inaccessibility of toiletries during travel; unavailability of cleansing products during emergency/urgent requirements; and inconveniences associated with using solids (soaps).

Accordingly, there is a need in the art to provide compositions/products which address the above-mentioned limitations of commercially available soap bars and liquid soap based cleansing products and at the same time, they should also be non-toxic by virtue of the selection of chemical ingredients used in the saponification process. More particularly, considering the above limitations, there is a need for a single time usage cleansing formulation, preferably a unit dosage formulation.

DESCRIPTION OF THE DISCLOSURE

The present disclosure aims to overcome the aforesaid drawbacks by providing an efficient saponification free solid cleansing composition for cleansing the skin, along with other advantages.

The present disclosure particularly relates to a saponification free cleansing composition.

More particularly, the present disclosure relates to a saponification free cleansing composition comprising at least one cleansing agent optionally along with adsorbing agent, excipient or a combination thereof.

As used herein, the terms/expressions "composition", "cleansing composition", "a saponification free solid cleansing composition", "saponification free cleansing composition", "solid cleansing composition" and related terminologies are employed interchangeably within the instant disclosure and refer to the composition of the present disclosure comprising at least one cleansing agent optionally along with adsorbing agent, excipient or a combination thereof.

As used herein, the terms/expressions "deodorizing agent" and "antimicrobial agent" are employed interchangeably within the instant disclosure and refer to agents/compounds which at least possess antimicrobial activity/function.

As used herein, the term "saponification" has a meaning as employed/understood in the field of soap preparation process. For instance, "saponification" involves reacting triglycerides with sodium or potassium hydroxide to produce glycerol and a fatty acid salt called 'soap'. Essentially, majority of the currently available/known cleansing compositions comprise soap as a primary or important ingredient. However, the present disclosure provides a cleansing/sanitizer composition or product which do not contain soap. Accordingly, the composition/product of the present disclosure is termed as a "saponification free cleansing composition".

As used herein, the terms "sanitization", "sanitizing" and related terminologies have a meaning as employed/understood in the field of general hygiene. In an embodiment, sanitization refers to destruction of most microorganisms (whether or not pathogenic) on human/animal skin, wounds, clothing or hard surfaces. In another embodiment, sanitization refers to the act or process of making something completely clean and free from microbes or bacteria.

In an embodiment of the present disclosure, the saponification free cleansing composition is a cosmeceutical composition or a pharmaceutical composition. In another embodiment, said composition is in a form selected from solid, liquid, foam, aerosol, or any combinations thereof. In yet another embodiment, the solid composition is formulated in a form selected from a group comprising tablet, capsule, pellet, spray dried material of various particle size distributions, liquid based product, foam or aerosol, powder, granule and bar. In yet another embodiment, the bars can be packed as blisters, strips, sachets, sprayers, dispensers, press/tap/slide-to-open containers, wraps and combinations thereof.

In an embodiment of the present disclosure, the cleansing agent is one or more surfactant(s), or a combination of one or more surfactant and one or more moisturizing agent(s).

In another embodiment of the present disclosure, the surfactant is selected from a group comprising synthetic surfactant, cationic surfactant, anionic surfactant, non-ionic surfactant, natural surfactant or semi-synthetic surfactant and combinations thereof.

In yet another embodiment of the present disclosure, the cationic surfactant is selected from a group comprising octenidine dihydrochloride, cetrimonium bromide (ctab), cetylpyridinium chloride (cpc), benzalkonium chloride, benzethonium chloride (bzt), dimethyldioctadecylammonium chloride, dioctadecyldimethylammonium bromide, dodecyl-, coco-, hexadecyl-, octadecyl, octadecyl/behenyl-, behenyl-, cocoamidopropyl-, trimethyl ammonium chloride-coco-, stearyl-, bis(2-hydroxyethyl)methyl ammonium chloride-benzalkonium chloride-alkyl, tetradecyl-, octadecyl-dimethyl benzyl ammonium chloride-dioctyl-, di(octyl-decyl)-, didecyl-, dihexadecyl-, distearyl-, di(hydrogenated tallow)-dimethyl ammonium chloride-di(hydrogenated tallow) benzyl, trioctyl-, tri (octyl-decyl)-, tridodecyl-, trihexadecyl-methyl ammonium chloride-dodecyl trimethyl-, dodecyl dimethyl benzyl-, di-(octyl-decyl) dimethyl, didecyl dimethylammonium bromide, amines with amide linkages quaternary ammonium salts, polyoxyethylene alkyl and alicyclic amines, N,N,N',N' tetrakis substituted ethylenediamines, 2-alkyl 1-hydroxethyl 2-imidazolines, and combinations thereof.

In still another embodiment of the present disclosure, the anionic surfactant is selected from a group comprising alkane sulfonates, sodium, ammonium, magnesium, sulfate, sulfonate, gluconate, Ammonium lauryl sulfate (ALS), sodium lauryl sulfate (sodium dodecyl sulfate, SLS, or SDS), and the related alkyl-ether sulfates such as sodium laureth sulfate (sodium lauryl ether sulfate or SLES), and sodium myreth sulfate, Docusate (dioctyl sodium sulfosuccinate), Perfluorooctanesulfonate (PFOS), Perfluorooctane Sulfonate, Alkyl-aryl ether phosphates, Alkyl ether phosphates, DDBSA (liquid and dry), Linear and Branched ALS, ALES, SLS, SLES, AOS—Calcium Alkyl Benzene Sulfonate (CABS)-Phosphate Esters, Disodium Lauroampho Diacetate, Acyl sarcosines, Acyl isethionates, Alkyl imidazolines, Alkyl sulfosuccinates, Amino acid-based or sugar based Glucoside, Sodium Cocoyl Hydrolyzed Wheat Protein, carboxylates. sulphonates, petroleum sulphonates, alkylbenzenesulphonates, naphthalenesulphonates, olefin sulphonates, alkyl sulphates, sulphates, sulphated esters, sulphated alkanolamides, alkylphenols, ethoxylated and sulphated compounds, and combinations thereof.

In still another embodiment of the present disclosure, the non-ionic surfactant is selected from a group comprising ethoxylates, alkoxylates cocamide both linear alcohol ethoxylates, branched alcohol ethoxylates, Fatty alcohol ethoxylates (Narrow-range ethoxylate, Octaethylene glycol monododecyl ether, Pentaethylene glycol monododecyl ether) Alkylphenol ethoxylates (Nonoxynols, Triton® X-100), Fatty acid ethoxylates, Special ethoxylated fatty esters and oils, Ethoxylated amines and/or fatty acid amides (Polyethoxylated tallow amine, Cocamide monoethanolamine, Cocamide diethanolamine), Terminally blocked ethoxylates (Poloxamers) Fatty acid esters of polyhydroxy compounds, Fatty acid esters of glycerol (Glycerol monostearate), Glycerol monolaurate), Fatty acid esters of sorbitan (Spans® & Tweens™), Fatty acid esters of sucrose, Alkyl polyglucosides (Decyl glucoside, Lauryl glucoside, Octyl glucoside), Amine oxides (Lauryldimethylamine oxide), Sulfoxides (Dimethyl sulfoxide) Phosphine oxides (Phosphine oxide), Alkyl Phenol Ethoxylates (NPE's and OPE's)—Castor Oil Ethoxylates and Hydrogenated Castor Oil Ethoxylates (CO-5, CO-16, CO-25, CO-36, CO-40, HCO-16, HCO-25, HCO-36, HCO-40)—Tallow Amine Ethoxylates (TAM-2, TAM-8, TAM-15, etc)—Natural and Synthetic Alcohol Ethoxylates—C6-C20 Alcohol Ethoxylates—Alcohol Ethoxylate Blends-NPE replacements—Secondary Alcohol Ethoxylates—PEG's (Polyethylene Glycols)-Polysorbates (20, 40, 60, 80) (Tweens™ (Ethoxylated), Spans® (Not Ethoxylated))-Oleyl Amine Ethoxylates-Coco Amine Ethoxylates—Stearyl Amine Ethoxylates—EO/PO Block Polymers-Coco-, Oleic-, Stearic-, Tall Oil Fatty-Acid Ethoxylates—Cocamide MEA, DEA, MIPA, ethoxylated aliphatic alcohol, polyoxyethylene surfactants, carboxylic esters, polyethylene glycol esters, anhydrosorbitol ester or it's ethoxylated derivatives carboxylic amides, monoalkanolamine condensates, polyoxyethylene fatty acid amides, and combinations thereof.

In still another embodiment of the present disclosure, the amphoteric surfactant is selected from a group comprising betaines, amine oxides, Coco Betaine, Cocamidopropyl Betaine, Lauryl Dimethylamine Oxide, Coco Alkyl Dimethyl Amine Oxides and combinations thereof.

In still another embodiment of the present disclosure, the natural surfactant is selected from a group comprising Soap Berries, Aritha, Soapwort, Castile Soap, *Yucca* Extract, Soapwort, Quillaja Bark Extract and combinations thereof.

In still another embodiment of the present disclosure, the semi-synthetic surfactant is selected from a group comprising glucoside derivatives, coconut oil derivatives, sulphated natural oils or fats, glycol esters of fatty acids, phosphatidiyl choline, sodium taurocholate and combinations thereof.

In an embodiment of the present disclosure, the moisturizing agent is selected from a group comprising glycerin, 4-Ethyl Resorcinol (Er), 4-Hexyl Resorcinol (Hr), Glycerin, Urea, Pyrrolidone Carboxylic Acid (Pca), Hydroxyethyl Urea, Hydrolyzed Keratin, Guar Hydroxypropyltrimonium Chloride, Panthenol, Polyglyceryl-3 Methylglucose Distearate, Sodium Hyaluronate Crosspolymer, Alpha Glucan Oligosaccharide, Ceramide 3, Betaine, Inulin, Butylene Glycol, Propylene Glycol, 3-Hexenol, polyglycerin-3, *lactobacillus*/milk ferment lysate filtrate, xylityl glucoside, polyols, ceramides, hyaluronic Acid, fatty acids, proteins, urea, alpha-hydroxy acids (AHAs), silicone, polysorbate 20 and combinations thereof.

In an embodiment of the present disclosure, the cleansing agent is selected from a group comprising cocamidopropyl betaine, sodium cocoyl isethionate, capryl glucoside, sodium cocoyl taurate and combinations thereof.

In an embodiment of the present disclosure, the surfactant is selected from a group comprising cocamidopropyl betaine, sodium cocoyl isethionate, capryl glucoside, sodium cocoyl taurate, glycosides, lauryl sulfates, amino acids derivatives, polysorbates, dimethylaminopropylamines and combinations thereof.

In another embodiment of the present disclosure, the cleansing agent is a combination of cocamidopropyl betaine, capryl glucoside, sodium cocoyl taurate and glycerine.

In another embodiment of the present disclosure, the cleansing agent is a combination of cocamidopropyl betaine, sodium cocoyl isethionate, sodium cocoyl taurate and glycerine.

In an embodiment of the present disclosure, the adsorbing agent is selected from a group comprising magnesium alumino meta silicate, colloidal silicon dioxide, alkali earth metal metasilicate, veegum, clay starch derived from corn, potato, peas, either non gelatinized partially gelatinized, or fully gelatinised, Calcium chloride, Calcium sulphate, Magnesium aluminum silicate, montmorillonite, clay, Talc maltodextrin, starch & its derivatives, Magnesium carbonates, Aluminium Hydroxide, Bentonite, Kaolin, attapulgite- and combinations thereof.

In a preferred embodiment of the present disclosure, the adsorbing agent is magnesium aluminometasilicate.

In an embodiment of the present disclosure, the excipient is selected from a group comprising skincare ingredient, deodorizing agent, foaming agent, Filler, disintegrant/super disintegrant, perfuming agent, chelating agent, solvent, preservative and combinations thereof.

In another embodiment of the present disclosure, the skin care agent is selected from a group comprising ethylhexylglycerin, above mentioned surfactants, above mentioned moisturizing agents and combinations thereof.

In yet another embodiment of the present disclosure, the deodorizing agent is selected from a group comprising ethylhexylglycerin, Imidazolidinyl Urea, Diazolidinyl Urea, DMDM Hydantoin, Sodium Hydroxymethylglycinate, Methylparaben, Propylene Glycol, Ethylparaben, Dehydroacetic acid, Phenoxyethanol, Iodopropynyl, Butylcarbamate, Potassium Sorbate, Benzoic acid, Sodium Benzoate, Benzyl Alcohol, Glyceryl Caprylate, Glyceryl Undecylenate, Propanediol, Caprylyl Glycol, Chlorphenesin, Phenethyl Alcohol, Pentylene Glycol,1,2-Benzisothiazol-3-one (BIT),5-bromo-5-nitro-1,3-dioxane, 2-bromo-2 nitropropane-1,3-diol, Chloroacetamide, Glutaraldehyde, Guanidine, hexamethylene-, homopolymer, 2-Methyl-2H-isothiazol-3-one (MI), Sodium hydroxy methyl glycinate, o-Phenylphenol, ethyldibromoglutaronitrile, Sodium nitrite, N-(3-Aminopropyl)-N-dodecylpropane-1,3-diamine, Phenoxy-ethanol, Triclosan, Phenoxypropanol, Sorbate and sorbic acid, Silver nitrate, Benzalkonium chloride, Benzethonium chloride, Cetrimonium bromide, Cetrimonium chloride, Cetylpyridinium, Cetrimide, Benzoxonium chloride, Didecyldimethylammonium chloride, Sodium hypochlorite, Tosylchloramide, octenidine, octenidine hydrochloride, and combinations thereof.

In still another embodiment of the present disclosure, the composition comprises sodium benzoate at a concentration ranging from about 0.1% w/w to 0.5% w/w.

In still another embodiment of the present disclosure, the composition comprises deodorizing agents methyl paraben and propyl paraben in combination, wherein the concentration methyl paraben is 0.18% w/w and the concentration propyl paraben is 0.02% w/w.

In still another embodiment of the present disclosure, the foaming agent is selected from a group comprising decyl polyglucoside, sodium cocoyl Apple, Sodium Cocoyl Sarcosinate, TEA Cocoyl Sarcosinate, Sodium Lauroyl Methylaminopropionate, Sodium Methyl Myristoyl Taurate, Sodium Lauryl Phosphate, Sodium Trideceth-4 Carboxylate, Trideceth-4 Carboxylic Acid, Sodium Cocomonoglyceride Sulfate, Sodium C14-16 Olefin Sulfonate, Sodium Cocoamphoacetate and combinations thereof.

In still another embodiment of the present disclosure, the filler is selected from a group comprising Maize starch B, Starch and its derivatives, Powdered Cellulose & its derivatives, Microcrystalline Cellulose, Calcium Phosphate or its derivatives, Lactose, Magnesium Aluminometasilicate, and combinations thereof.

In still another embodiment of the present disclosure, the filler is adjuvant, wherein the said adjuvant increases the bulkiness of the product with or without specific roll.

In still another embodiment of the present disclosure, the disintegrant/super disintegrants is selected from a group comprising sodium starch glycolate, cross-linked polyvinylpyrrolidone (crospovidone XL 10), Crosslinked cellulose, Croscarmellose and its salts, Crosslinked PVP, Crosslinked starch, Sodium Starch Glycolate, sodium lauryl sulphates, Crosslinked alginic acid, Alginic acid NF, Alginates, Pectins, Carrageenan, Carbopol or its derivatives, Natural super Disintegrants, Soy polysaccharides, polysaccharides and its derivatives, Ion exchange resins, Anionic resin, cationic resins, formalin casein, chitin, chitosan, polymerized agar acrylamide, xylan, smecta, key-jo-clay, crosslinked carboxymethyl guar, modified tapioca starch, and Calcium Silicate and combinations thereof.

In still another embodiment of the present disclosure, the perfuming agent is selected from a group comprising natural perfuming agent, natural identical perfuming agent, artificial perfuming agent and combinations thereof.

In still another embodiment of the present disclosure, the perfuming agent is selected from a group comprising citrus perfuming agent, orange perfuming agent, strawberry perfuming agent, lomania perfuming agent, lemon perfuming agent, strawberry, neem, peach, apple, mint, lavender, peach, bubblegum, cherry, black currant, avocado, raspberry, sandalwood, champa, jasmine, rose, *eucalyptus*, lemon grass, water melon and combinations thereof.

In still another embodiment of the present disclosure, the solvent is selected from a group comprising propylene glycol, Ethanol, Isopropyl Alcohol, Glycerin, PEG 300/400/600, PEG 1000, PEG 3000, Benzyl alcohol, Polysorbates, water and combinations thereof, wherein the concentration of solvent ranges from 0 to 30% w/w.

In still another embodiment of the present disclosure, the chelating agent is disodium edetate.

The present disclosure further relates to a saponification free solid cleansing composition comprising at least one cleansing agent, adsorbing agent, skin care agent, deodorizing/antimicrobial agent, foaming agent, filler, perfuming agent, chelating agent and disintegrant/super disintegrant.

The present disclosure further relates to a saponification free solid cleansing composition comprising surfactant, adsorbing agent, foaming agent, skin care agent, deodorizing agent, Moisturizing agent, filler, disintegrant/super disintegrant, chelating agent and perfuming agent.

The present disclosure further relates to a saponification free solid cleansing composition comprising surfactant, foaming agent, skin care agent, deodorizing agent, moisturizing agent, filler, disintegrant/super disintegrant, chelating agent and perfuming agent.

The present disclosure further relates to a saponification free solid cleansing composition comprising adsorbing agent, foaming agent, skin care agent, deodorizing agent, Moisturizing agent, filler, disintegrant/super disintegrant, chelating agent and perfuming agent.

The present disclosure further relates to a saponification free solid cleansing composition comprising surfactant, adsorbing agent, skin care agent, deodorizing agent, Moisturizing agent, filler, disintegrant/super disintegrant, chelating agent and perfuming agent.

The present disclosure further relates to a saponification free solid cleansing composition comprising surfactant, adsorbing agent, foaming agent, deodorizing agent, Moisturizing agent, filler, disintegrant/super disintegrant, chelating agent and perfuming agent.

The present disclosure further relates to a saponification free solid cleansing composition comprising surfactant, adsorbing agent, foaming agent, skin care agent, Moisturizing agent, filler, disintegrant/super disintegrant, chelating agent and perfuming agent.

The present disclosure further relates to a saponification free solid cleansing composition comprising surfactant, adsorbing agent, foaming agent, skin care agent, deodorizing agent, filler, disintegrant/super disintegrant, chelating agent and perfuming agent.

The present disclosure further relates to a saponification free solid cleansing composition comprising surfactant, adsorbing agent, foaming agent, skin care agent, deodorizing agent, moisturizing agent, disintegrant/super disintegrant, chelating agent and perfuming agent.

The present disclosure further relates to a saponification free solid cleansing composition comprising surfactant, adsorbing agent, foaming agent, skin care agent, deodorizing agent, moisturizing agent, filler, chelating agent and perfuming agent.

The present disclosure further relates to a saponification free solid cleansing composition comprising surfactant, adsorbing agent, foaming agent, skin care agent, deodorizing agent, moisturizing agent, filler, disintegrant/super disintegrant, and perfuming agent.

The present disclosure further relates to a saponification free solid cleansing composition comprising surfactant, adsorbing agent, foaming agent, skin care agent, deodorizing agent, moisturizing agent, filler, disintegrant/super disintegrant and chelating agent.

In an embodiment of the present disclosure, the cleansing agent is present at a concentration ranging from about 0% w/w to 90% w/w. In a preferred embodiment of the present disclosure, the concentration of cleansing agent is ranging from 10 to 50% w/w. In another preferred embodiment of the present disclosure, the concentration of cleansing agent is about 26% w/w.

In an embodiment of the present disclosure, the surfactant is present at a concentration ranging from about 0% w/w to 90% w/w. In another embodiment of the present disclosure, the surfactant is present at a concentration ranging from about 5% w/w to 50% w/w. In a preferred embodiment of the present disclosure, the concentration of surfactant is about 26% w/w.

In an embodiment of the present disclosure, the cocamido propyl betaine is present at a concentration ranging from about 0% w/w to 90% w/w. In another embodiment of the present disclosure, the cocamido propyl betaine is present at a concentration ranging from about 5% w/w to 50% w/w. In a preferred embodiment of the present disclosure, the concentration of cocamido propyl betaine is about 43% w/w. In another preferred embodiment of the present disclosure, the concentration of cocamido propyl betaine is about 26% w/w.

In an embodiment of the present disclosure, the capryl glucoside is present at a concentration ranging from about 0% w/w to 90% w/w. In another embodiment of the present disclosure, the capryl glucoside is present at a concentration ranging from about 5% w/w to 50% w/w. In a preferred embodiment of the present disclosure, the concentration of capryl glucoside is about 43% w/w. In another preferred embodiment of the present disclosure, the concentration of capryl glucoside is about 26% w/w.

In an embodiment of the present disclosure, the sodium cocoyl isethionate is present in the composition at a concentration ranging from about 0% w/w to 90% w/w. In another embodiment of the present disclosure, the sodium cocoyl isethionate is present at a concentration ranging from about 5% w/w to 50% w/w. In a preferred embodiment of the present disclosure, the concentration of sodium cocoyl isethionate is about 43% w/w. In another preferred embodiment of the present disclosure, the concentration of sodium cocoyl isethionate is about 26% w/w.

In an embodiment of the present disclosure, the sodium methyl cocoyl taurate is present at a concentration ranging from about 0% w/w to 90% w/w. In another embodiment of the present disclosure, the sodium cocoyl taurate is present at a concentration ranging from about 5% w/w to 50% w/w. In a preferred embodiment of the present disclosure, the concentration of sodium cocoyl taurate is about 43% w/w. In another preferred embodiment of the present disclosure, the concentration of sodium cocoyl taurate is about 26% w/w.

In an embodiment of the present disclosure, the moisturizing agent is present at a concentration ranging from about 0.2% w/w to 30% w/w. In a preferred embodiment of the present disclosure, the concentration of moisturizing agent is about 6% w/w. In another preferred embodiment of the present disclosure, the concentration of moisturizing agent is about 2% w/w. In yet another preferred embodiment of the present disclosure, the concentration of moisturizing agent is about 3% w/w.

In an embodiment of the present disclosure, the glycerin is present at a concentration ranging from about 1% w/w to 25% w/w. In another embodiment of the present disclosure, the glycerin is present at a concentration ranging from about 1% w/w to 9% w/w. In a preferred embodiment of the present disclosure, the concentration of glycerin is about 4% w/w.

In an embodiment of the present disclosure, the xylityl glucoside is present at a concentration ranging from about 0.1% w/w to 30% w/w. In a preferred embodiment of the present disclosure, the concentration of xylityl glucoside is about 2% w/w. In another preferred embodiment of the present disclosure, the concentration of xylityl glucoside is about 3% w/w.

In an embodiment of the present disclosure, the adsorbing agent is present at a concentration ranging from about 1% w/w to 50% w/w. In a preferred embodiment of the present disclosure, the concentration of adsorbing agent is about 30% w/w.

In an embodiment of the present disclosure, the magnesium aluminometasilicate is present in the composition at a concentration ranging from about 1% w/w to 50% w/w. In a preferred embodiment of the present disclosure, the concentration of magnesium aluminometasilicate is about 18% w/w. In another preferred embodiment of the present disclosure, the concentration of magnesium aluminometasilicate is about 30% w/w.

In an embodiment of the present disclosure, the skin care agent is present at a concentration ranging from about 0.01% w/w to 10% w/w. In a preferred embodiment of the present disclosure, the concentration of skin care agent is about 0.03% w/w. In another embodiment of the present disclosure, the concentration of skin care agent is about 1.14% w/w.

In an embodiment of the present disclosure, the deodorizing agent is present at a concentration ranging from about 0.001% w/w to 5% w/w. In another embodiment of the present disclosure, the deodorizing agent is present at a concentration ranging from about 0.01% w/w to 3% w/w. In a preferred embodiment of the present disclosure, the concentration of deodorizing agent is about 0.2% w/w. In another preferred embodiment of the present disclosure, the concentration of deodorizing agent is about 0.03% w/w. In yet another preferred embodiment of the present disclosure, the concentration of deodorizing agent is about 1.15% w/w.

In an embodiment of the present disclosure, the ethylhexylglycerin is present at a concentration ranging from about 0.01% w/w to 10% w/w. In a preferred embodiment of the present disclosure, the concentration of ethylhexylglycerin is about 0.03% w/w.

In an embodiment of the present disclosure, the Octenidine HCl is present at a concentration ranging from about 0.01% w/w to 10% w/w. In a preferred embodiment of the present disclosure, the concentration of Octenidine HCl is about 0.03% w/w.

In an embodiment of the present disclosure, the solvent is present at a concentration ranging from about 0% w/w to 50% w/w. In another embodiment of the present disclosure, the solvent is present at a concentration ranging from about 0.5% w/w to 50% w/w. In yet another embodiment of the present disclosure, the solvent is present at a concentration ranging from about 0.5% w/w to 30% w/w. In a preferred embodiment of the present disclosure, the concentration of solvent is about 10% w/w.

In an embodiment of the present disclosure, the propylene glycol is present at a concentration ranging from about 1% w/w to 50% w/w. In a preferred embodiment of the present disclosure, the concentration of propylene glycol is about 5% w/w.

In an embodiment of the present disclosure, the foaming agent is present at a concentration ranging from about 0% w/w to 90% w/w. In another embodiment of the present disclosure, the foaming agent is present at a concentration ranging from about 4% w/w to 50% w/w. In a preferred embodiment of the present disclosure, the concentration of foaming agent is about 4% w/w. In another preferred embodiment of the present disclosure, the concentration of foaming agent is about 5.88% w/w. In yet another preferred embodiment of the present disclosure, the concentration of foaming agent is about 6% w/w.

In an embodiment of the present disclosure, the decyl polyglucoside is present at a concentration ranging from about 0% w/w to 90% w/w. In another embodiment of the present disclosure, the decyl polyglucoside is present at a concentration ranging from about 4% w/w to 50% w/w. In a preferred embodiment of the present disclosure, the concentration of decyl polyglucoside is about 2% w/w. In a preferred embodiment of the present disclosure, the concentration of decyl polyglucoside is about 3% w/w. In an exemplary embodiment of the present disclosure, the concentration of decyl polyglucoside is about 3.07% w/w.

In an embodiment of the present disclosure, the sodium cocoyl apple is present at a concentration ranging from about 4% w/w to 50% w/w. In a preferred embodiment of the present disclosure, the concentration of sodium cocoyl apple is about 2% w/w. In another preferred embodiment of the present disclosure, the concentration of sodium cocoyl apple is about 3% w/w.

In an embodiment of the present disclosure, the filler is present at a concentration ranging from about 1% w/w to 60% w/w. In a preferred embodiment of the present disclosure, the concentration of filler is about 30% w/w.

In an embodiment of the present disclosure, the maize starch B is present at a concentration ranging from about 1% w/w to 60% w/w. In a preferred embodiment of the present disclosure, the concentration of maize starch B is about 30% w/w. In a preferred embodiment of the present disclosure, the concentration of maize starch B is about 37% w/w. In an exemplary embodiment of the present disclosure, the concentration of maize starch B is about 36.83% w/w.

In an embodiment of the present disclosure, the disintegrant/super disintegrant is present at a concentration ranging from about 1% w/w to 30% w/w. In a preferred embodiment of the present disclosure, the concentration of disintegrant/super disintegrant is about 5% w/w. In another preferred embodiment of the present disclosure, the concentration of disintegrant/super disintegrant is about 8% w/w. In yet another preferred embodiment of the present disclosure, the concentration of disintegrant/super disintegrant is about 11% w/w. In still another preferred embodiment of the present disclosure, the concentration of disintegrant/super disintegrant is about 14% w/w. In an exemplary embodiment of the present disclosure, the concentration of disintegrant/super disintegrant is about 13.48% w/w.

In an embodiment of the present disclosure, the sodium starch glycolate is present at a concentration ranging from about 1% w/w to 30% w/w. In a preferred embodiment of the present disclosure, the concentration of sodium starch glycolate is about 5% w/w. In another preferred embodiment of the present disclosure, the concentration of sodium starch glycolate is about 8% w/w. In yet another preferred embodiment of the present disclosure, the concentration of sodium starch glycolate is about 11% w/w. In still another preferred embodiment of the present disclosure, the concentration of sodium starch glycolate is about 14% w/w. In an exemplary embodiment of the present disclosure, the concentration of sodium starch glycolate is about 13.48% w/w.

In an embodiment of the present disclosure, the cross-linked polyvinylpyrrolidone (crospovidone XL 10) is present at a concentration ranging from about 1% w/w to 30% w/w. In a preferred embodiment of the present disclosure, the concentration of cross-linked polyvinylpyrrolidone (crospovidone XL 10) is about 5% w/w.

In another preferred embodiment of the present disclosure, the concentration of cross-linked polyvinylpyrrolidone (crospovidone XL 10) is about 8% w/w. In yet another preferred embodiment of the present disclosure, the concentration of cross-linked polyvinylpyrrolidone (crospovidone XL 10) is about 11% w/w. In still another preferred embodiment of the present disclosure, the concentration of cross-linked polyvinylpyrrolidone (crospovidone XL 10) is about 14% w/w. In an exemplary embodiment of the present disclosure, the concentration of cross-linked polyvinylpyrrolidone (crospovidone XL 10) is about 13.48% w/w.

In an embodiment of the present disclosure, the perfuming agent is present at a concentration ranging from about 0% w/w to 10% w/w. In a preferred embodiment of the present disclosure, the concentration of perfuming agent is about 1% w/w. In an exemplary embodiment of the present disclosure, the concentration of perfuming agent is about 0.75% w/w.

In an embodiment of the present disclosure, the citrus perfuming agent is present at a concentration ranging from about 0.01% w/w to 5% w/w. In a preferred embodiment of the present disclosure, the concentration of citrus perfuming agent is about 1% w/w. In an exemplary embodiment of the present disclosure, the concentration of citrus perfuming agent is about 0.75% w/w.

In an embodiment of the present disclosure, the chelating agent is present at a concentration ranging from about 0% w/w to 5% w/w. In a preferred embodiment of the present disclosure, the concentration of chelating agent is about 1% w/w.

In an embodiment of the present disclosure, the disodium edetate is present at a concentration ranging from about 0% w/w to 5% w/w. In a preferred embodiment of the present disclosure, the concentration of disodium edetate is about 0.5% w/w.

In an embodiment of the present disclosure, the above composition comprises moisture content ranging from 0 to 50% w/w. In another embodiment of the present disclosure, the above composition optionally comprises moisture content ranging from 10% w/w to 20% w/w. In a preferred embodiment of the present disclosure, the above composition optionally comprises moisture content ranging from 0.25% w/w to 25% w/w.

In an embodiment of the present disclosure, the present composition comprises 0.25 to 25% w/w moisture to formulate the composition in solid form. In another embodiment of the present disclosure, the present composition comprises more than 25% w/w moisture to formulate the composition in liquid, foam or aerosol form.

In an embodiment of the present disclosure, the total parts of the components in the composition add up to 100% w/w.

In an embodiment of the present disclosure, the excipient is selected from a group comprising skincare ingredient, deodorizing agent, foaming agent, filler, disintegrant/super disintegrant, perfuming agent, solvent, preservant and combinations thereof.

In another embodiment of the present disclosure, the excipients comprise a combination of ethylhexylglycerin (skin care agent), octenidine HCl (deodorizing agent/antimicrobial agent), and propylene glycol or isopropylene glycol. In particular, the synergistic combination of these ingredients provide good efficacy to the composition.

The present disclosure further relates to a saponification free solid cleansing composition comprising cleansing agent at a concentration of about 0 to 90% w/w, adsorbing agent at a concentration of about 1% w/w to 50% w/w, skin care agent at a concentration of about 0.01% w/w to 10% w/w, deodorizing agent at a concentration of about 0.001% w/w to 5% w/w, foaming agent at a concentration of about 0 to 90% w/w, filler at a concentration of about 1% w/w to 60% w/w, disintegrant/super disintegrant at a concentration of about 1% w/w to 30% w/w, chelating agent at a concentration ranging from about 0% w/w to 5% w/w and perfuming agent at a concentration of about 0% w/w to 10% w/w, wherein the concentrations of both surfactant and foaming agent should not be '0' in the composition; and where in the total parts of the components in the composition add up to 100% w/w.

In an embodiment of the present disclosure, the above composition optionally comprises moisture content ranging from 0.25% w/w to 50% w/w. In another embodiment of the present disclosure, the above composition optionally comprises moisture content ranging from 10% w/w to 20% w/w.

In an embodiment of the present disclosure, the present composition comprises 0.25 to 25% w/w moisture to formulate the composition in solid form. In another embodiment of the present disclosure, the present composition comprises more than 25% w/w moisture to formulate the composition in liquid, foam or aerosol form.

The present disclosure further relates to a saponification free solid cleansing composition comprising surfactant at a concentration of about 5% w/w to 50% w/w, adsorbing agent at a concentration of about 1% w/w to 50% w/w, skin care agent at a concentration of about 0.01% w/w to 10% w/w, deodorizing agent at a concentration of about 0.001% w/w to 5% w/w, foaming agent at a concentration of about 4% w/w to 50% w/w, filler at a concentration of about 1% w/w to 60% w/w, disintegrant/super disintegrant at a concentration of about 1% w/w to 30% w/w, chelating agent at a concentration ranging from about 0% w/w to 5% w/w and perfuming agent at a concentration of about 0.01% w/w to 10% w/w, wherein the concentrations of both surfactant and foaming agent should not be '0' in the composition; and wherein the total parts of the components in the composition add up to 100% w/w.

In an embodiment of the present disclosure, the above composition optionally comprises moisture content ranging from 0.25% w/w to 30% w/w. In another embodiment of the present disclosure, the above composition optionally comprises moisture content ranging from 2% w/w to 20% w/w.

In a preferred embodiment of the present disclosure, the above composition optionally comprises moisture content ranging from 0.25% w/w to 25% w/w.

The present disclosure further relates to a saponification free solid cleansing composition comprising surfactant at a concentration of about 26% w/w, moisturizing agent at a concentration of about 6% w/w, adsorbing agent at a concentration of about 30% w/w, skin care agent at a concentration of about 0.03% w/w, deodorizing agent at a concentration of about 0.03% w/w, foaming agent is 4% w/w, chelating agent at a concentration of about 1% w/w, filler at a concentration of about 30% w/w, disintegrant/super disintegrant at a concentration of about 11% w/w, and perfuming agent at a concentration of about 1% w/w, wherein the concentrations of both surfactant and foaming agent should not be '0' in the composition; and wherein the total parts of the components in the composition add up to 100% w/w.

The present disclosure further relates to a saponification free solid cleansing composition comprising cleansing agent at a concentration of about 0 to 90% w/w, skin care agent at a concentration of about 0.01% w/w to 10% w/w, deodorizing agent at a concentration of about 0.001% w/w to 5% w/w, foaming agent at a concentration of about 0 to 90% w/w, filler at a concentration of about 1% w/w to 60% w/w, disintegrant/super disintegrant at a concentration of about 1% w/w to 30% w/w, chelating agent at a concentration ranging from about 0% w/w to 5% w/w and perfuming agent at a concentration of about 0.01% w/w to 10% w/w, wherein the concentrations of both surfactant and foaming agent should not be '0' in the composition; and wherein the total parts of the components in the composition add up to 100% w/w.

The present disclosure further relates to a saponification free solid cleansing composition comprising surfactant at a concentration of about 37% w/w, moisturizing agent at a concentration of about 6% w/w, skin care agent at a concentration of about 0.03% w/w, deodorizing agent at a concentration of about 0.03% w/w, foaming agent is 4% w/w, filler at a concentration of about 34% w/w, disintegrant/super disintegrant at a concentration of about 19% w/w, chelating agent at a concentration of about 1% w/w and perfuming agent at a concentration of about 1% w/w, wherein the concentrations of both surfactant and foaming agent should not be '0' in the composition; and wherein the total parts of the components in the composition add up to 100% w/w.

The present disclosure further relates to a saponification free solid cleansing composition comprising surfactant at a concentration of about 43% w/w, moisturizing agent at a concentration of about 6% w/w, skin care agent at a concentration of about 0.03% w/w, deodorizing agent at a concentration of about 0.03% w/w, foaming agent at a concentration of about 7% w/w, filler at a concentration of about 34% w/w, disintegrant/super disintegrant at a concentration of about 19% w/w and perfuming agent at a concentration of about 1% w/w, chelating agent is present at a concentration ranging from about 0% w/w to 5% w/w, wherein the concentrations of both surfactant and foaming agent should not be '0' in the composition; and wherein the total parts of the components in the composition add up to 100% w/w.

In an embodiment of the present disclosure, the above mentioned saponification free solid cleansing composition is a cosmeceutical or pharmaceutical composition, and wherein said composition is in a form selected from a group comprising tablets, capsules, pellets, spray dried materials of various particle size distributions, liquid based products, foams or aerosols, powders, granules, bars which can be packed as blisters, strips, sachets, sprayers, dispensers, press/tap/slide-to-open containers, wraps and combinations thereof.

In an embodiment, the components of the instant saponification free cleansing composition come together and there is a synergistic interplay between the components which interact to perform specific roles/functions important for producing the saponification free cleansing composition.

The disclosure provides process of preparing said composition and its applications for cleansing the skin and/or inanimate objects.

The compositions provided by the present disclosure is useful for cleansing the skin, paediatric, geriatric or veterinary, washing of utensils and cloths requiring more than regular level of cleanliness, expensive stationery articles, getting rid of sticky materials from surfaces, potentiation of routinely used detergents.

In an embodiment of the present disclosure, the saponification free cleansing composition provided herein offers several potential advantages, some of which include: Environment friendly, User friendly, Economical, Easily accessible, Convenient to use, Meant for single application, Portability, Easy availability, New form of cleansing product, Versatility of presentation, Easy way to maintain hygiene, and Wide scope from relevance point of view including prevention of wide spread occurrence of an epidemic or contaminated disease.

The present disclosure also relates to a process for preparing saponification free cleansing composition.

In a non-limiting embodiment of the present disclosure, the process for preparing saponification free cleansing composition comprising at least one cleansing agent and excipient(s) comprises the step of mixing cleansing agent and excipient(s) to obtain the saponification free cleansing composition.

In a non-limiting embodiment of the present disclosure, the process for preparing saponification free cleansing composition comprising at least one cleansing agent and excipient comprising at least one antimicrobial agent comprises the step of mixing cleansing agent and the excipient comprising antimicrobial agent to obtain the saponification free cleansing composition.

In a non-limiting embodiment of the present disclosure, the process for preparing saponification free cleansing composition comprising at least one cleansing agent, adsorbing agent and excipient(s) comprises the step of mixing cleansing agent and adsorbing agent followed by mixing of the excipient(s) to obtain the saponification free cleansing composition.

In a non-limiting embodiment of the present disclosure, the process for preparing saponification free cleansing composition comprising at least one surfactant and excipient(s) comprises the step of mixing surfactant and the excipient(s) to obtain the saponification free cleansing composition.

In a non-limiting embodiment of the present disclosure, the process for preparing saponification free cleansing composition comprising at least one surfactant, adsorbing agent and excipient(s) comprises the step of mixing surfactant and adsorbing agent followed by mixing of the excipient(s) to obtain the saponification free cleansing composition.

In another non-limiting embodiment of the present disclosure, the process further comprises a combination of unit operations such as granulation (wet or dry), drying, spray drying, milling/sizing, mixing, solubilization, wet milling, colloidal milling, homogenization, air jet milling, compaction, hot-melt extrusion, extrusion-spheronisation, compaction and any other unit operation required for the form of presentation of the end product such as tablets, capsules, pellets, spray dried materials of various particle size distributions, liquid based products, foams or aerosols, powders, granules, bars which can be packed as blisters, strips, sachets, sprayers, dispensers, press/tap/slide-to-open containers or wraps.

In yet another non-limiting embodiment of the present disclosure, the steps of grinding/pulverizing, mixing and sieving to obtain the final product, wherein said grinding, mixing steps are carried out in a rapid mixer granulator or mass mixer (followed by roller compactor), double cone blender or any apparatus capable of performing these functions; wherein said sieving is carried out in #40 ASTM Mesh.

In still another non-limiting embodiment of the present disclosure, grinding is carried out to obtain a mesh size ranging from about #8 to #80, preferably a mesh size of about #40. In another preferred embodiment, grinding is carried out to obtain a mesh size of about #30.

In a non-limiting embodiment, the composition of the present disclosure is in a coarse to fine granular/powder form.

In an exemplary embodiment of the present disclosure, the process for preparing saponification free solid cleansing composition (provided in below table 1) comprises the following steps:

TABLE 1

Saponification free solid cleansing composition of the present disclosure

| Sl. No. | Component | Quantity |
|---|---|---|
| 1 | Adsorbing agent | 1% w/w to 50% w/w |
| 2 | Surfactant | 0% w/w to 90% w/w |
| 3 | Moisturizing agent | 0.2% w/w to 30% w/w |
| 4 | skincare agent | 0.01% w/w to 10% w/w |
| 5 | deodorizing agent | 0.001% w/w to 5% w/w |
| 6 | Foaming agent | 0% w/w to 90% w/w |
| 7 | Filler | 1% w/w to 60% w/w |
| 8 | Disintegrant/super disintegrant | 1% w/w to 30% w/w |
| 9 | Perfuming agent | 0% w/w to 10% w/w |
| 10 | Chelating agent | 0% w/w to 5% w/w |
| 11 | Solvent | 0% w/w to 50% w/w. |

Note:
total parts of the components in the composition add up to 100% w/w.

Manufacturing Procedure 1 [Liquid Components Mixed and Adsorbed Using Adsorbing Agent to Obtain a Solid/Powder Form Composition]

Step 1: Surfactant, moisturizing agent, solvent, skincare agent, deodorizing agent, chelating agent, foaming agent and perfuming are mixed together to form a Mixture 1.

Step 2: Mixture 1 obtained from step 1 is blended with an adsorbing agent and allowed to adsorb for about minimum 60 minutes under continuous mixing until to form free flowing powder using rapid mixer granulator or mass mixer (followed by roller compactor-if required) to obtain Mixture 2.

Step 3: Mixture 2 obtained from step 2 is passed through #40 ASTM Mesh to obtain Mixture 3.

Step 4: Filler is added to the Mixture 3 obtained from step 3 and mixed for about 30 minutes in a double cone blender or mass mixer to obtain Mixture 4.

Step 5: Disintegrant/super disintegrant is added additionally to the mixture 4 obtained from step 4 and mixed for about 15 minutes or until uniform mixture forms in a double cone blender or mass mixer to obtain Mixture 5.

Step 6: Mixture 5 obtained from step 5 is compressed into tablets followed by packing into blisters, strips, containers or sachets.

OR

Mixture 5 obtained from step 5 is converted into pellets followed by filling into hard gelatin/cellulosic capsules.

OR

Mixture 5 obtained from step 5 is filled into sachets, hard gelatin/cellulosic capsules.

In an exemplary embodiment of the present disclosure, the process for preparing saponification free solid cleansing composition (provided in below table 2) comprises the following steps:

TABLE 2

Saponification free solid cleansing composition of the present disclosure

| Sl. No. | Component | Quantity |
|---|---|---|
| 1 | Surfactant | 0% w/w to 90% w/w |
| 2 | Moisturizing agent | 0.2% w/w to 30% w/w |
| 3 | skincare agent | 0.01% w/w to 10% w/w |
| 4 | deodorizing agent | 0.001% w/w to 5% w/w |
| 5 | Foaming agent | 0% w/w to 90% w/w |
| 6 | Filler | 1% w/w to 60% w/w |
| 7 | Disintegrant/super disintegrant | 1% w/w to 30% w/w |
| 8 | Perfuming agent | 0% w/w to 10% w/w |
| 9 | Chelating agent | 0% w/w to 5% w/w |
| 10 | Solvent | 0% w/w to 50% w/w. |

Note:
the total parts of the components in the composition add up to 100% w/w.

Manufacturing Procedure 2 [Liquid Components Spray Dried to Obtain Flowable Solid/Powder Mass Composition]

Step 1: Surfactant, Moisturizing agent, solvent, skincare agent, chelating agent, deodorizing agent and or Foaming agent and perfuming agent are mixed together to form Mixture 1a.

Step 2: Mixture 1a from step 1 is spray dried to obtain spray dried powder/granules.

Step 3: Filler is added to the spray dried powder/granules obtained from step 2, mixed for adequate time in a double cone blender or mass mixer to obtain Mixture 2a.

Step 4: Disintegrant/super disintegrant is added additionally to the Mixture 2a obtained from step 3 and mixed for about 15 minutes or more in a double cone blender to obtain the saponification free solid composition Mixture 3a.

Step 5: Mixture 3 obtained from step 4 is compressed into tablets followed by packing into blisters, strips, containers or sachets.

OR

Mixture 3 obtained from step 4 is converted into pellets followed by filling into hard gelatin/cellulosic capsules.

OR

Mixture 3 obtained from step 4 is filled into sachets, hard gelatin/cellulosic capsules.

In another exemplary embodiment of the present disclosure, the process for preparing saponification free solid cleansing composition (provided in below table 3) comprises the following steps described in Manufacturing Procedure 1 or Manufacturing Procedure 2:

TABLE 3

Saponification free solid cleansing composition of the present disclosure

| Sl. No. | Component | Quantity (mg/Unit) |
|---|---|---|
| 1 | Adsorbing agent | 150 |
| 2 | Surfactant | 110 |
| 3 | Moisturizing agent | 8 |
| 4 | Solvent | 9 |
| 5 | skincare agent | 0.075 |
| 6 | deodorizing agent | 0.075 |
| 7 | Foaming agent | 20 |
| 8 | Filler | 146 |
| 9 | Disintegrant/ super disintegrant | 58 |
| 10 | Perfuming agent | 3 |

Manufacturing Procedure 1

Step 1: Surfactant, moisturizing agent, solvent, skincare agent, deodorizing agent, chelating agent, foaming agent, perfuming agent are mixed together to form a Mixture 1.

Step 2: Mixture 1 obtained from step 1 is blended with an adsorbing agent and allowed to adsorb for 60 minutes under continuous mixing using rapid mixer granulator or mass mixer (followed by roller compactor-if required) to obtain Mixture 2.

Step 3: Mixture 2 obtained from step 2 is passed through #40 ASTM Mesh to obtain Mixture 3.

Step 4: Filler is added to the Mixture 3 obtained from step 3 and mixed for about 30 minutes or more in a double cone blender or mass mixer to obtain Mixture 4.

Step 5: Disintegrant/super disintegrant is added additionally to the mixture 4 obtained from step 4 and mixed for about 15 minutes or more in a double cone blender or mass mixer to obtain Mixture 5.

Step 6: Mixture 5 obtained from step 5 is compressed into tablets followed by packing into blisters, strips, containers or sachets.

OR

Mixture 5 obtained from step 5 is converted into pellets followed by filling into hard gelatin/cellulosic capsules.

OR

Mixture 5 obtained from step 5 is filled into sachets, hard gelatin/cellulosic capsules.

Manufacturing Procedure 2

Step 1: Surfactant, Moisturizing agent, solvent, skincare agent, deodorizing agent and or Foaming agent and or perfuming agent are mixed together to form a Mixture 1.

Step 2: Mixture 1 from step 1 is spray dried to obtain spray dried powder/granules.

Step 3: Filler is added to the spray dried powder/granules obtained from step 2, mixed for adequate time in a double cone blender or mass mixer to obtain Mixture 2.

Step 4: Disintegrant/super disintegrant is added additionally to the Mixture 2 obtained from step 3 and mixed for about 15 minutes or more in a double cone blender to obtain Mixture 3.

Step 5: Mixture 3 obtained from step 4 is compressed into tablets followed by packing into blisters, strips, containers or sachets.

OR

Mixture 3 obtained from step 4 is converted into pellets followed by filling into hard gelatin/cellulosic capsules.

OR

Mixture 3 obtained from step 4 is filled into sachets, hard gelatin/cellulosic capsules.

In yet another exemplary embodiment of the present disclosure, the process for preparing saponification free solid cleansing composition (provided in Table 4) comprises the following steps:

TABLE 4

Saponification free solid cleansing composition of the present disclosure

| Sl. No | Component | Quantity (mg/Unit) |
|---|---|---|
| 1 | Surfactant | 110 |
| 2 | Moisturizing agent | 8 |
| 3 | Solvent | 0 |
| 4 | skincare agent | 0.15 |
| 5 | deodorizing agent | 0.15 |
| 6 | Foaming agent | 20 |
| 7 | Filler | 146 |
| 8 | Disintegrant/super disintegrant | 58 |
| 9 | Perfuming agent | 3 |

Manufacturing Procedure 3 [all Components Present in Solid/Powder Form and the Process Comprises Mixing the Components to Obtain the Composition (No Adsorbing Agent or Spray Drying Required)]

Step 1: Surfactant, moisturizing agent, solvent, skincare agent, deodorizing agent, foaming agent, disintegrant/super disintegrant and filler are mixed together in a double cone/octagonal Blender for about 15 to 20 minutes to form a Mixture 1.

Step 2: Mixture 1 obtained from step 1 is compressed into tablets followed by packing into blisters, strips, containers or sachets.

OR

Mixture 1 obtained from step 1 is converted into pellets followed by filling into hard gelatin/cellulosic capsules.

OR

Mixture 1 obtained from step 1 is filled into sachets, hard gelatin/cellulosic capsules.

In an embodiment of the present disclosure, the present saponification free solid cleansing composition comprising about 10% w/w to 60% w/w of surfactant (a single surfactant or a combination of surfactants), either with or without foaming agent provide desired/better cleaning efficacy.

In another embodiment of the present disclosure, the present saponification free solid cleansing composition comprising about 10% w/w to 60% w/w of surfactant and 2 to 20% w/w foaming agent provides better froth formation.

In an exemplary embodiment of the present disclosure, the present saponification free solid cleansing composition comprises about 10% w/w to 60% w/w of surfactant (a single surfactant or a combination of surfactants), antimicrobial agent or deodorizing agent, optionally along with adsorbing agent and/or other excipients to provide desired/better removal of microbial load.

In yet another embodiment of the present disclosure, the present saponification free solid cleansing composition comprises about 1 to 25% w/w of disintegrants. In another embodiment, the present saponification free solid cleansing composition comprises disintegrants and said composition in the form of unit dosage form (eg. tablet) disintegrates within 1 to 180 seconds. In yet another embodiment, without disintegrants, the present saponification free solid cleansing composition in the form of tablet will not disintegrate within 1 to 180 seconds.

In yet another embodiment of the present disclosure, the present saponification free solid cleansing composition comprises moisture at a concentration of about 0.25% w/w to 25% w/w, preferably about 0.25% w/w to 25% w/w. Said moisture content is necessary to result in the tablet form of the composition.

In a non-limiting embodiment, the composition of the present disclosure is packed in a suitable container/package system in a quantity required to meet the commercial and cosmetic needs.

In another non-liming embodiment, the composition is packed in a 0.2 gram, 0.3 gram, 0.4 gram, 0.5 gram, 1 gram, 5 grams, 10 grams, 100 grams or 500 grams containers to meet the commercial and cosmetic needs.

The present disclosure further relates to the use of the saponification free solid cleansing composition as described above for cleansing applications. In an embodiment of the present disclosure, the saponification free solid cleansing composition has applications in cleansing skin, cleansing inanimate objects, paediatric application, geriatric or veterinary application, washing of utensils or clothes, cleansing stationary articles, getting rid of sticky material(s) from surfaces, potentiation of routinely used detergents, or any combination of applications thereof to reduce the microbial load.

In an exemplary embodiment of the present disclosure, the saponification free solid cleansing composition is employed for cleansing/sanitizing human or animal skin, or cleansing/sanitizing inanimate objects or surfaces.

The present disclosure thus provides saponification free cleaning product which is a unique dosage form, which can be accessed with ease, primarily for personal/self hygiene. Such increased hygiene provided by the presently disclosed cleansing composition/unit dosage form can eliminate/retard the spread of any contagious disease including the coronavirus based pandemic cases such as COVID-19.

EXAMPLES

Example 1: Solid Cleansing Compositions

Following ingredients and quantities as shown in the below Table 5 were employed for preparing saponification free solid cleansing compositions.

TABLE 5

| Sl. No. | Component | Quantity (mg/unit) |
|---|---|---|
| 1 | Magnesium aluminometasilicate | 1% w/w to 50% w/w |
| 2 | cocamidopropyl betaine | 0% w/w to 90% w/w |
| 3 | Capryl glucoside | 0% w/w to 90% w/w |
| 4 | Sodium cocoyl taurate | 0% w/w to 90% w/w |
| 5 | Glycerin | 0.2% w/w to 30% w/w |
| 6 | Propylene glycol | 0.5% w/w to 30% w/w |
| 7 | Ethylhexylglycerin | 0.01% w/w to 10% w/w |
| 8 | Octenidine Hcl | 0.001% w/w to 5% w/w |
| 9 | Xylityl glucoside | 0.2% w/w to 30% w/w |
| 10 | Decyl polyglucoside | 0% w/w to 90% w/w |
| 11 | Sodium cocoyl Apple | 0% w/w to 90% w/w |
| 12 | Maize starch B | 1% w/w to 60% w/w |
| 13 | Sodium starch glycolate | 1% w/w to 30% w/w |
| 14 | Crospovidone XL 10 | 1% w/w to 30% w/w |
| 15 | Perfuming agent | 0% w/w to 10% w/w |
| 16 | Di sodium edetate | 0% w/w to 5% w/w |

Note:
the total parts of the components in the composition add up to 100% w/w.

Example 2: Exemplary Solid Cleansing Composition

An exemplary/specific saponification free solid cleansing composition was prepared with the quantities of components as shown in the below Table 6.

TABLE 6

| Sl. No. | Ingredients | mg/unit | % w/w |
|---|---|---|---|
| 1 | Magnesium aluminometasilicate | 150.000 | 30.364 |
| 2 | Cocamidopropyl betaine | 110.000 | 22.267 |
| 3 | Capryl glucoside | | |
| 4 | Sodium cocoyl taurate | | |
| 5 | Decyl Polyglucoside | 10.000 | 2.024 |
| 6 | sodium cocoyl apple | 10.000 | 2.024 |
| 7 | Ethylhexylglycerin | | |
| 8 | Propylene glycol | 0.150 | 0.030 |
| 9 | Octenidine HCl | | |
| 10 | Xylityl Glucoside | 7.750 | 1.569 |
| 11 | Maize starch B | 145.900 | 29.534 |
| 12 | Sodium Starch Glycolate | 25.000 | 5.061 |
| 13 | Crospovidone XL 10 | 32.500 | 6.579 |
| 14 | Perfuming agent | 2.700 | 0.547 |

Example 3: Procedure for Preparing Compositions of Example 1

The composition disclosed in example 1 can be prepared by either of the two manufacturing procedures described below.

Manufacturing Procedure 1

Step 1: cocamidopropyl betaine, capryl glucoside, sodium cocoyl taurate, Sodium EDTA, Glycerin, Propylene Glycol, Ethylhexylglycerin, Octenidine HCl, Xylityl Glucoside, Decyl Polyglucoside, Sodium cocoyl Apple and perfuming agent are mixed together to form a mixture 1b.

Step 2: Mixture 1b obtained from step 1 is blended Magnesium Aluminometasilicate and allowed to adsorb for 60 minutes under continues mixing using rapid mixer granulator or mass mixer (followed by roller compactor-if required) to obtain mixture 2b.

Step 3: Mixture 2b obtained from step 2 is passed through #40 ASTM Mesh to obtain mixture 3b.

Step 4: Maize starch B is added to the mixture 3b obtained from step 3 and mixed for 30 minutes in a double cone blender or mass mixer to obtain mixture 4b.

Step 5: Sodium Starch Glycolate and cross-linked polyvinylpyrrolidone (crospovidone XL 10) is added to the mixture 4b obtained from step 4 and mixed for 15 minutes in a double cone blender or mass mixer to obtain solid free cleansing composition mixture 5b.

Step 6: Mixture 5b obtained from step 5 is compressed into tablets followed by packing into blisters, strips, containers or sachets.

OR

Mixture 5b obtained from step 5 is converted into pellets followed by filling into hard gelatin/cellulosic capsules.

OR

Mixture 5b obtained from step 5 is filled into sachets, hard gelatin/cellulosic capsules.

Manufacturing Procedure 2

Step 1: cocamidopropyl betaine, capryl glucoside, sodium cocoyl taurate, Glycerin, Propylene Glycol, Ethylhexylglycerin, Octenidine HCl, Xylityl Glucoside, Decyl Polyglucoside, Sodium cocoyl Apple and perfuming agent are mixed together to form a Mixture 1c.

Step 2: Magnesium Aluminometasilicate is mixed with the Mixture 1c obtained from step 1 in a double cone blender to obtain Mixture 2c.

Step 3: Maize starch B is added to the Mixture 2c obtained from step 2 mixed for 30 minutes in a double cone blender or mass mixer to obtain Mixture 3c.

Step 4: Sodium Starch Glycolate and cross-linked polyvinylpyrrolidone (Crospovidone XL 10) are added to the Mixture 3c obtained from step 3 and mixed for 15 minutes in a double cone blender to obtain Mixture 4c.

Step 5: Mixture 4c obtained from step 4 is compressed into tablets followed by packing into blisters, strips, containers or sachets.

OR

Mixture 4c obtained from step 4 is converted into pellets followed by filling into hard gelatin/cellulosic capsules.

OR

Mixture 4c obtained from step 4 is filled into sachets, hard gelatin/cellulosic capsules.

Example 4: Dosage Form Comprising Solid Cleansing Composition

Another specific dosage form (tablet) comprising the saponification free solid cleansing composition was prepared with components and respective quantities as shown in the below Table 8. The different processes for preparing the same is further described below.

TABLE 8

| Sl. No. | Ingredients | mg/unit | % w/w |
|---|---|---|---|
| 1 | Cocamidopropyl betaine | 110.000 | 36.667 |
| 2 | Capryl glucoside | | |
| 3 | Sodium cocoyl taurate | | |
| 4 | Decyl Polyglucoside | 10.000 | 3.333 |
| 5 | sodium cocoyl apple | 10.000 | 3.333 |
| 6 | Propylene glycol | 0.200 | 0.067 |
| 7 | Ethylhexylglycerin | | |
| 8 | Octenidine Hcl | | |
| 9 | Xylityl Glucoside | 7.750 | 2.583 |
| 10 | Maize starch B | 101.850 | 33.950 |
| 11 | Sodium Starch Glycolate | 25.000 | 8.333 |
| 12 | Crospovidone XL 10 | 32.500 | 10.833 |
| 13 | Perfuming agent | 2.700 | 0.900 |

Procedure 1 for Preparing Composition of Table 8

Step 1: Cocamidopropyl betaine, capryl glucoside, sodium cocoyl taurate, Glycerin, Propylene Glycol, Ethylhexylglycerin, Octenidine HCl, Xylityl Glucoside, Decyl Polyglucoside, Sodium cocoyl Apple, Maize starch B, Sodium Starch Glycolate, cross-linked polyvinylpyrrolidone (Crospovidone XL 10) and perfuming agent are mixed together in a double cone/Octagonal Blender for 15 to 20 minutes to form a Mixture 1d.

Step 2: Mixture 1d obtained from step 1 is compressed into tablets followed by packing into blisters, strips, containers or sachets.

OR

Mixture 1d obtained from step 1 is converted into pellets followed by filling into hard gelatin/cellulosic capsules.

OR

Mixture 1d obtained from step 1 is filled into sachets, hard gelatin/cellulosic capsules.

Procedure 2 for Preparing Composition of Table 8

Step 1: Cocamido propyl betaine, capryl glucoside, sodium cocoyl taurate, Sodium EDTA Glycerin, Propylene Glycol, Ethylhexylglycerin, Octenidine HCl, Xylityl Glucoside, Decyl Polyglucoside, Sodium cocoyl Apple, and perfuming agent are mixed together to form a Mixture 1e.

Step 2: Mixture 1e from step 1 is spray dried to obtain spray dried powder/granules.

Step 3: Maize Starch B is added to the spray dried powder/granules obtained from step 2, mixed for adequate time in a double cone blender or mass mixer to obtain Mixture 2e.

Step 4: Sodium Starch Glycolate, cross-linked polyvinylpyrrolidone (Crospovidone XL 10) are added additionally to the Mixture 2e obtained from step 3 and mixed for 15 minutes in a double cone blender to obtain saponification free solid composition Mixture 3e.

Step 5: Mixture 3e obtained from step 4 is compressed into tablets followed by packing into blisters, strips, containers or sachets.

OR

Mixture 3e obtained from step 4 is converted into pellets followed by filling into hard gelatin/cellulosic capsules.

OR

Mixture 3e obtained from step 4 is filled into sachets, hard gelatin/cellulosic capsules.

Example 5: Efficacy Study

AS-P-001 is a saponification free solid cleansing composition of the present disclosure. Components and their concentrations according to AS-P-001 is provided in table 9 below. AS-P-002 and AS-P-003 are comparative compositions containing concentrations of components outside the range of the concentrations of the present composition.

TABLE 9

Compositions AS-P-001, AS-P-002 and AS-P-003

| S. No. | Material Name | AS-P-001 mg/unit (mg) | % w/w | AS-P-002 mg/unit (mg) | % w/w | AS-P-003 mg/unit (mg) | % w/w |
|---|---|---|---|---|---|---|---|
| 1 | Mg. Aluminometasilicate | 70.00 | 17.90 | 70.00 | 20.16 | 70.00 | 21.51 |
| 2.1 | Cocamidopropyl Betaine | 31.25 | 7.99 | 18.75 | 5.40 | 12.50 | 3.84 |
| 2.2 | Sodium methyl cocoyl taurate | 30.65 | 7.84 | 18.39 | 5.30 | 12.26 | 3.77 |
| 2.3 | Sodium Cocoyl Isethionate | 20.00 | 5.12 | 12.00 | 3.46 | 8.00 | 2.46 |
| 3 | PG + EHG + OHCl | 4.45 | 1.14 | 2.67 | 0.77 | 1.78 | 0.55 |
| 4 | Xylityl Glucoside | 12.00 | 3.07 | 12.00 | 3.46 | 12.00 | 3.69 |
| 5 | Decyl Polyglucoside | 12.00 | 3.07 | 7.20 | 2.07 | 4.80 | 1.48 |
| 6 | sodium cocoyl apple | 11.00 | 2.81 | 6.60 | 1.90 | 4.40 | 1.35 |
| 7 | Maize starch B | 144.00 | 36.83 | 144.00 | 41.47 | 144.00 | 44.25 |
| 8 | Sodium Starch Glycolate | 26.00 | 6.65 | 26.00 | 7.49 | 26.00 | 7.99 |
| 9 | Crospovidone XL 10 | 26.70 | 6.83 | 26.70 | 7.69 | 26.70 | 8.21 |
| 10 | Perfume (citrus fragrance) | 2.95 | 0.75 | 2.95 | 0.85 | 2.95 | 0.91 |
| | Total Weight | 391.00 | 100.00 | 347.26 | 100.00 | 325.39 | 100.00 |

Experimental study was conducted to evaluate the antibacterial activity of AS-P-001, AS-P-002 and AS-P-003 compositions against *Staphylococcus aureus* and *Pseudomonas aeruginosa* bacterial Strains (both strains *Staphylococcus aureus* ATCC® 6538™ (Generic name: *Staphylococcus aureus* subsp. *Aureus*) and *Pseudomonas aeruginosa* ATCC®15442 ™ (Generic name: *Pseudomonas aeruginosa* (Schroeter) Migula) were sourced from ATCC, USA).

Observations/Results

Post incubation of the bacterial cultures (24 hours treatment) with AS-P-001, AS-P-002 and AS-P-003, AS-P-001 showed 99.9% reduction bacterial load in comparison to initial bacterial load in treated samples (both *Staphylococcus aureus* and *Pseudomonas aeruginosa* plates) when compared to untreated samples (both 0 and 24 hours)—see Table 10. However, AS-P-002 and AS-P-003 showed a lesser/inferior reduction in bacterial count.

Inference

The results from the study confirms that, under the testing conditions applied, AS-P-001 showed an excellent 99.9% reduction in bacterial count when compared to AS-P-002 and AS-P-003 composition which contained same components but with different concentrations. Thus, it can be concluded that the present saponification free solid cleansing composition (eg. AS-P-001) shows excellent antimicrobial/antibacterial activity, thereby indicating its high utility as a cleansing/sanitizing product.

The above provided comparative study also demonstrates the synergistic effect of the combination of all the ingredients and respective concentrations/ranges as defined in the present disclosure in achieving excellent/superior antimicrobial/antibacterial efficacy and thereby cleansing efficiency. In particular, the interplay between the ingredients and the concentrations of the ingredients in the saponification free solid cleansing composition plays a crucial role leading to excellent efficacy as discussed above.

TABLE 10

Antibacterial activity

| Sl. No | Sample | Test bacterium | Contact Time (Total Viable Count) 0 h | 24 h | Reduction Against Initial Log10 | % |
|---|---|---|---|---|---|---|
| 1 | AS-P-001 | *Staphylococcus aureus* | 100500 | 75 | 1.88 | 99.93 |
| 2 | | *Pseudomonas aeruginosa* | 99333 | 17 | 1.23 | 99.98 |
| 1 | AS-P-002 | *Staphylococcus aureus* | 100500 | 4600 | 3.66 | 95.00 |
| 2 | | *Pseudomonas aeruginosa* | 99333 | 4550 | 3.66 | 95.00 |
| 1 | AS-P-003 | *Staphylococcus aureus* | 100500 | 11667 | 4.07 | 88.39 |
| 2 | | *Pseudomonas aeruginosa* | 99333 | 13600 | 4.13 | 86.31 |

In addition to the above described antibacterial study, experiments to study cleansing efficiency were conducted as per the established guidelines with respect to the composition AS-P-001. Said experimental study passed the cleaning efficiency test.

Furthermore, experiments on safety study (skin irritation study) was conducted as per the established guidelines to demonstrate the safety aspects of the composition AS-P-001. Said experimental study passed the safety features.

Example 6: Comparative Study on Various Formulations Indicating the Importance of Present Saponification Free Solid Cleansing Composition The following Table 11 describes compositions of the present disclosure. Compositions 11A, 11B, 11C and 11D describe comparative compositions.

Following observations can be made based on the above Table 11:

1) In the present compositions, magnesium aluminometasilicate is greater than 15% w/w (about 25% w/w and 20% w/w, respectively). However, it was observed that if the employed concentration of magnesium aluminometasilicate concentration was less than 15% w/w and components under Sl. Nos. 2, 3, 4, 5 and 6 are in liquid form, then the composition was not suitable for tableting. In particular, such compositions did not form tablets, and the granules were wet.

2) Based on composition 11A it was observed that in the absence of adsorbent (magnesium aluminometasilicate) and if the surfactants were provided in liquid form, the compo-

TABLE 11

| Sl. No | Ingredients | Function | Present Composition 1 mg/unit | Present Composition 1 % w/w | Present Composition 2 mg/unit | Present Composition 2 % w/w | Composition 11A mg/unit | Composition 11A % w/w |
|---|---|---|---|---|---|---|---|---|
| 1 | Magnesium Aluminometasilicate | Adsorbant | 118.8 | 24.8 | 90 | 19.9 | 0 | 0 |
| 2 | Cocamidopropyl Betaine (CAPB) + Caprylyl/Capryl Glucoside (CG) + Sodium Methyl Cocoyl Taurate | Surfactant | 122.5 | 25.5 | 122.5 | 27.1 | 122.5 | 33.9 |
| 3 | Propylene glycol + Ethylhexylglycerin + Octenidine dihydrochloride | Antimicrobial agent | 0.3 | 0.1 | 0.3 | 0.1 | 0.3 | 0.1 |
| 4 | Xylityl Glucoside | Moisturizing agent | 8.5 | 1.8 | 8.5 | 1.9 | 8.5 | 2.4 |
| 5 | Decyl Polyglucoside | Foaming agent | 15 | 3.1 | 15 | 3.3 | 15 | 4.2 |
| 6 | Sodium cocoyl Apple | Foaming agent | 17.5 | 3.6 | 17.5 | 3.9 | 17.5 | 4.8 |
| 7 | Maize starch B | Filler | 136 | 28.3 | 136 | 30.1 | 136 | 37.7 |
| 8 | Sodium Starch Glycolate | Disintegrant | 25 | 5.2 | 25 | 5.5 | 25 | 6.9 |
| 9 | Crospovidone XL 10 | Disintegrant | 32.4 | 6.8 | 32.4 | 7.2 | 32.4 | 9.0 |
| 10 | Perfume | Perfume | 4 | 0.8 | 4 | 0.9 | 4 | 1.1 |
|  | Total weight |  | 480 | 100 | 451.2 | 100 | 361.2 | 100 |

| Sl. No. | Ingredients | Function | Composition 11C mg/unit | Composition 11C % w/w | Composition 11D mg/unit | Composition 11D % w/w | Composition 11B mg/unit | Composition 11B % w/w |
|---|---|---|---|---|---|---|---|---|
| 1 | Magnesium Aluminometasilicate | Adsorbant | 118.8 | 33.2 | 118.8 | 26.5 | 118.8 | 28.1 |
| 2 | Cocamidopropyl Betaine (CAPB) + Caprylyl/Capryl Glucoside(CG) + Sodium Methyl Cocoyl Taurate | Surfactant | 0 | 0 | 122.5 | 27.4 | 122.5 | 29.0 |
| 3 | Propylene glycol + Ethylhexylglycerin + Octenidine dihydrochloride | Antimicrobial agent | 0.3 | 0.1 | 0.3 | 0.1 | 0.3 | 0.1 |
| 4 | Xylityl Glucoside | Moisturizing agent | 8.5 | 2.4 | 8.5 | 1.9 | 8.5 | 2.0 |
| 5 | Decyl Polyglucoside | Foaming agent | 15 | 4.2 | 0 | 0 | 15 | 3.5 |
| 6 | Sodium cocoyl Apple | Foaming agent | 17.5 | 4.9 | 0 | 0 | 17.5 | 4.1 |
| 7 | Maize starch B | Filler | 136 | 38.0 | 136 | 30.4 | 136 | 32.2 |
| 8 | Sodium Starch Glycolate | Disintegrant | 25 | 7.0 | 25 | 5.6 | 0 | 0.0 |
| 9 | Crospovidone XL 10 | Disintegrant | 32.4 | 9.1 | 32.4 | 7.2 | 0 | 0.0 |
| 10 | Perfume | Perfume | 4 | 1.1 | 4 | 0.9 | 4 | 0.9 |
|  | Total weight |  | 357.5 | 100 | 447.5 | 100 | 422.6 | 100 | sition obtained by mixing the ingredients did not form free flowing powder and wet lumps were observed.

3) The present composition comprises disintegrants. However, based on composition 11B, it was observed that in the absence of disintegrants such as sodium starch glycolate and cross-linked polyvinylpyrrolidone (crospovidone XL 10), the tablet does not disintegrate in 1 to 180 seconds thereby indicating the importance of disintegrant in the composition. Further, experimental studies revealed that disintegrants at a concentration ranging from about 2 to 25% are required for preparing efficient saponification free solid cleansing compositions according to the present disclosure.

4) Based on the present compositions, it was observed that the composition forms foam efficiently in the presence of combination of surfactants (CAPB, CG and CT) along with foaming agents (sodium cocoyl Apple and decyl polyglucoside). However, based on compositions 11C and 11D, it was observed that if a single surfactant or a single foaming agent is employed, or if the composition lacks a surfactant or a foaming agent, the desired efficiency is not achieved. Thus, a combination of agents including combination of surfactants or foaming agents, or a combination of surfactant and foaming agent is required to achieve the desired cleansing efficacy.

5) The present compositions comprise foaming agents. Based on composition 11D, it was observed that the composition does not form foam efficiently if foaming agents (sodium cocoyl apple and decyl polyglucoside) are not present in the composition. Further, it was also observed that if the foaming agents (sodium cocoyl apple and decyl polyglucoside) are not present, the composition forms foam bubbles which are larger in size with harder texture.

Further, additional experiments were also conducted and the summary/results of the same are as follows:

6) Experimental studies were conducted to establish the importance with respect to the size of the granules of the composition. Studies revealed that granules of Mesh 14 to 80 are crucial for preparing different dosage forms of the saponification free cleansing composition including all unit dosage forms, tablets etc.

7) Experimental studies were conducted to establish the importance with respect to the moisture content of the granules of the composition. Studies revealed that maintaining a moisture content between 0.25 to 25% is essential for preparing different dosage forms of the saponification free cleansing composition including all unit dosage forms, tablets etc.

8) Additional experimental studies were conducted to establish the importance with respect to the surfactant concentration in the composition. Studies revealed that 10 to 60% w/w of a single surfactant or a combination of surfactants give better cleansing efficacy with or without foaming agents. Further, it was also observed that the aforesaid surfactants along with foaming agent at a concentration range of about 2 to 30% w/w give better froth formation.

9) Experimental studies were conducted to establish the importance with respect to the surfactant concentration in the composition. Studies revealed that 10 to 60% w/w of a single surfactant or a combination of surfactants along with at least one antimicrobial agent/deodorizing agent and with/ without foaming agents give better cleansing and germ kill efficacy. Further, it was also observed that the aforesaid surfactants along with foaming agent at a concentration range of about 2 to 30% w/w give better froth formation.

Additional embodiments and features of the present disclosure will be apparent to one of ordinary skill in art based upon description provided herein. The embodiments herein provide various features and advantageous details thereof in the description. Descriptions of well-known/conventional methods and techniques are omitted so as to not unnecessarily obscure the embodiments herein. Further, the disclosure herein provides for examples illustrating the above described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

The foregoing description of the specific embodiments reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this disclosure have been described in terms of preferred embodiments, those skilled in the art will recognize that the embodiments herein can be practiced with modification within the spirit and scope of the embodiments as described herein.

Throughout this specification, the word "comprise", or variations such as "comprises" or "comprising" or "including" wherever used, will be understood to imply the inclusion of a stated element, integer or step, or group of elements, integers or steps, but not the exclusion of any other element, integer or step, or group of elements, integers or steps.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

NUMBERED EMBODIMENTS OF THE DISCLOSURE

1) A saponification free cleansing composition comprising a cleansing agent optionally along with adsorbing agent, excipient or a combination thereof; wherein the cleansing agent is one or more surfactant or a combination of one or more surfactant and one or more moisturizing agent.

2) The saponification free cleansing composition of embodiment 1, wherein the surfactant is selected from a group comprising synthetic surfactant, cationic surfactant, anionic surfactant, non-ionic surfactant, natural surfactant, semi-synthetic surfactant and combinations thereof;
and the excipient is selected from a group comprising skincare agent, deodorizing agent, foaming agent, filler, disintegrant or super disintegrant, perfuming agent, chelating agent, solvent, preservative and combinations thereof.

3) The saponification free cleansing composition of embodiment 1 or embodiment 2, wherein said composition comprises a cleansing agent and excipient optionally along with adsorbing agent; wherein the cleansing agent is one or more surfactant and the excipient comprises one or more deodorizing agent or antimicrobial agent,
or said composition comprises cleansing agent, adsorbing agent, skin care agent, deodorizing agent or antimicrobial agent, foaming agent, filler, perfuming agent, chelating agent, disintegrant or super disintegrant, and perfuming agent.

4) The saponification free cleansing composition of any of the above embodiments, wherein said composition comprises cleansing agent at a concentration ranging from about 0 to 90% w/w, adsorbing agent at a concentration ranging from about 1% w/w to 50% w/w, skin care agent at a concentration ranging from about 0.01% w/w to 10% w/w, deodorizing agent at a concentration ranging from about 0.001% w/w to 5% w/w, foaming agent at a concentration ranging from about 0 to 90% w/w, filler at a concentration ranging from about 1% w/w to 60% w/w, disintegrant or super disintegrant at a concentration ranging from about 1% w/w to 30% w/w, chelating agent at a concentration ranging from about 0% w/w to 5% w/w and perfuming agent at a concentration ranging from about 0% w/w to 10% w/w;
wherein the concentrations of both surfactant and foaming agent is not '0' in the composition; and wherein the total parts of the components in the composition add up to 100% w/w.

5) The saponification free cleansing composition of any of the above embodiments, wherein the surfactant is selected from a group comprising cocamidopropyl betaine, sodium cocoyl isethionate, capryl glucoside, sodium cocoyl taurate and combinations thereof;
the moisturizing agent is selected from a group comprising glycerine, 4-Ethyl Resorcinol (Er), 4-Hexyl Resorcinol (Hr), Glycerin, Urea, Pyrrolidone Carboxylic Acid (Pca), Hydroxyethyl Urea, Hydrolyzed Keratin, Guar Hydroxypropyltrimonium Chloride, Panthenol, Polyglyceryl-3 Methylglucose Distearate, Sodium Hyaluronate Crosspolymer, Alpha Glucan Oligosaccharide, Ceramide 3, Betaine, Inulin, Butylene Glycol, Propylene Glycol, 3-Hexenol, polyglycerin-3, *lactobacillus*/milk ferment lysate filtrate, xylityl glucoside, polyols, ceramides, hyaluronic Acid, fatty acids, proteins, urea, alphahydroxy acids (AHAs), silicone and combinations thereof;
the adsorbing agent is selected from a group comprising magnesium alumino meta silicate, colloidal silicon dioxide, alkali earth metal metasilicate, veegum, clay starch derived from corn, potato, peas, either non gelatinized partially gelatinized, or fully gelatinised, calcium chloride, calcium sulphate, magnesium aluminum silicate, montmorillonite, clay, talc maltodextrin, starch or its derivatives, magnesium carbonates, aluminium hydroxide, bentonite, kaolin, attapulgite and combinations thereof;
the skin care agent is selected from a group comprising ethylhexylglycerin, above mentioned surfactants, above mentioned moisturizing agents and combinations thereof;
the deodorizing agent is selected from a group comprising Ethylhexylglycerin, Imidazolidinyl Urea, Diazolidinyl Urea, DMDM Hydantoin, Sodium Hydroxymethylglycinate, Methylparaben, Propylene Glycol, Ethylparaben, Dehydroacetic acid, Phenoxyethanol, Iodopropynyl, Butylcarbamate, Potassium Sorbate, Benzoic acid, Sodium Benzoate, Benzyl Alcohol, Glyceryl Caprylate, Glyceryl Undecylenate, Propanediol, Caprylyl Glycol, Chlorphenesin, Phenethyl Alcohol, Pentylene Glycol, 1,2-Benzisothiazol-3-one (BIT),5-bromo-5-nitro-1,3-dioxane, 2-bromo-2 nitropropane-1, 3-diol, Chloroacetamide, Glutaraldehyde, Guanidine, hexamethylene-, homopolymer, 2-Methyl-2H-isothiazol-3-one (MI), Sodium hydroxy methyl glycinate, o-Phenylphenol, ethyldibromoglutaronitrile, Sodium nitrite, N-(3-Aminopropyl)-N-dodecylpropane-1,3-diamine, Phenoxy-ethanol, Triclosan, Phenoxypropanol, Sorbate and Sorbic acid, Silver nitrate, Benzalkonium chloride, Benzethonium chloride, Cetrimonium bromide, Cetrimonium chloride, Cetylpyridinium, Cetrimide, Benzoxonium chloride, Didecyldimethylammonium chloride, Sodium hypochlorite, Tosylchloramide, Octenidine, Octenidine hydrochloride and combinations thereof;
the foaming agent is selected from a group comprising Decyl polyglucoside, Sodium cocoyl apple, Sodium Cocoyl Sarcosinate, TEA Cocoyl Sarcosinate, Sodium Lauroyl Methylaminopropionate, Sodium Methyl Myristoyl Taurate, Sodium Lauryl Phosphate, Sodium Trideceth-4 Carboxylate, Trideceth-4 Carboxylic Acid, Sodium Cocomonoglyceride Sulfate, Sodium C14-16 Olefin Sulfonate, Sodium Cocoamphoacetate and combinations thereof;
the filler is selected from a group comprising Maize starch B, Starch or its derivatives, Powdered Cellulose or its derivatives, Microcrystalline Cellulose, Calcium Phosphate, Lactose, Magnesium Aluminometasilicate and combinations thereof;
the perfuming agent is selected from a group comprising citrus perfuming agent, orange perfuming agent, strawberry perfuming agent, lomania perfuming agent, lemon perfuming agent, strawberry, neem, peach, apple, mint, lavender, peach, bubblegum, cherry, black currant, avocado, raspberry, sandalwood, champa, jasmine, rose, *eucalyptus*, lemon grass, water melon and combinations thereof;
the chelating agent is disodium edetate; and
the disintegrant or super disintegrant is selected from a group comprising Sodium starch glycolate, cross-linked polyvinylpyrrolidone (Crospovidone XL 10), Crosslinked cellulose, Croscarmellose or its salts, Crosslinked PVP, Crosslinked starch, Sodium Starch Glycolate, Crosslinked alginic acid, Alginic acid NF, Alginates, Pectins, Carrageenan, Carbopol or its derivatives, Natural super disintegrants, Soy polysaccharides, Polysaccharides or its derivatives, Ion exchange resins, Anionic resin, Cationic resins, Formalin casein, Chitin, Chitosan, Polymerized agar acrylamide, Xylan, Smecta, Key-jo-clay, Crosslinked carboxymethyl Guar, Modified tapioca starch, Calcium silicate and combinations thereof.

6) The saponification free cleansing composition of any of the above embodiments, wherein:
the cleansing agent is a combination of cocamidopropyl betaine, sodium cocoyl isethionate, sodium cocoyl taurate and glycerine;
the adsorbing agent is magnesium aluminometasilicate;
the skin care agent is ethylhexylglycerin;
the deodorizing agent is a combination of ethylhexylglycerin, propylene glycol and octenidine dihydrochloride;
the foaming agent is a combination of decyl polyglucoside and sodium cocoyl apple;
the filler is Maize starch B;
the chelating agent is a disodium edetate;
the disintegrant is a combination of sodium starch glycolate and cross-linked polyvinylpyrrolidone (crospovidone XL 10); and
the perfuming agent is citrus perfuming agent, sandal wood, rose, berries, joy, lemon grass, mint, or any combination thereof.

7) The saponification free cleansing composition of any of the above embodiments, wherein the composition comprises magnesium aluminometasilicate, cocamidopropyl betaine, sodium methyl cocoyl taurate, sodium cocoyl isethionate, PG-EHG-OHCl (propylene glycol, ethylhexylglycerin, and octenidine HCl), xylityl glucoside, decyl polyglucoside, sodium cocoyl apple, maize starch b, sodium starch glycolate, cross-linked polyvinylpyrrolidone (crospovidone x1 10), and perfume.

8) The saponification free cleansing composition of any of the above embodiments, wherein said composition comprises magnesium aluminometasilicate at a concentration ranging from about 1% w/w to 50% w/w, cocamidopropyl betaine at a concentration ranging from about 0% w/w to 90% w/w, sodium cocoyl isethionate at a concentration ranging from about 0% w/w to 90% w/w, sodium cocoyl taurate at a concentration ranging from about 0% w/w to 90% w/w, glycerin at a concentration ranging from about 0.2% w/w to 30% w/w, propylene glycol at a concentration ranging from about 0.5% w/w to 30% w/w, ethylhexylglycerin at a concentration ranging from about 0.01% w/w to 10% w/w, octenidine HCl at a concentration ranging from about 0.001% w/w to 5% w/w, xylityl glucoside at a concentration ranging from about 0.2% w/w to 30% w/w, decyl polyglucoside at a concentration ranging from about 0% w/w to 90% w/w, sodium cocoyl apple at a concentration ranging from about 0% w/w to 90% w/w, maize starch b at a concentration ranging from about 1% w/w to 60% w/w, sodium starch glycolate at a concentration ranging from about 1% w/w to 30% w/w, cross-linked polyvinylpyrrolidone (Crospovidone x1 10) at a concentration ranging from about 1% w/w to 30% w/w, perfuming agent at a concentration ranging from about 0% w/w to 10% w/w, and di sodium edetate at a concentration ranging from about 0% w/w to 5% w/w;
and wherein the total parts of the components in the composition add up to 100% w/w.

9) The saponification free cleansing composition of any of the above embodiments, wherein said composition comprises:
magnesium aluminometasilicate at a concentration of about 17.90% w/w, cocamidopropyl betaine at a concentration of about 7.99% w/w, sodium methyl cocoyl taurate at a concentration of about 7.84% w/w, sodium cocoyl isethionate at a concentration of about 5.12% w/w, a combination of ethylhexylglycerin, propylene glycol and octenidine HCl at a concentration of about 1.14% w/w, xylityl glucoside at a concentration of about 3.07% w/w, decyl polyglucoside at a concentration of about 3.07% w/w, sodium cocoyl apple at a concentration of about 2.81% w/w, maize starch b at a concentration of about 36.83% w/w, sodium starch glycolate at a concentration of about 6.65% w/w, cross-linked polyvinylpyrrolidone (crospovidone x1 10) at a concentration of about 6.83% w/w, and perfume at a concentration of about 0.75% w/w;

or said composition comprises:
magnesium aluminometasilicate at a concentration of about 25% w/w, cocamidopropyl betaine at a concentration of about 15% w/w, sodium methyl cocoyl taurate at a concentration of about 8% w/w, cocoyl glycoside 7% at a concentration of about 8% w/w, a combination of ethylhexylglycerin, propylene glycol and octenidine HCl at a concentration of about 0.5% w/w, xylityl glucoside at a concentration of about 5% w/w, decyl polyglucoside at a concentration of about 3% w/w, sodium cocoyl apple at a concentration of about 3% w/w, maize starch b at a concentration of about 12.75% w/w, sodium starch glycolate at a concentration of about 7% w/w, cross-linked polyvinylpyrrolidone (crospovidone x1 10) at a concentration of about 5% w/w, and perfume at a concentration of about 0.75% w/w or said composition comprises:
magnesium aluminometasilicate at a concentration of about 30.36% w/w, a combination of cocamidopropyl betaine, sodium cocoyl taurate and capryl glucoside at a concentration of about 22.26% w/w, a combination of ethylhexylglycerin, propylene glycol and octenidine HCl at a concentration of about 0.03% w/w, xylityl glucoside at a concentration of about 1.56% w/w, decyl polyglucoside at a concentration of about 2.02% w/w, sodium cocoyl apple at a concentration of about 2.02% w/w, maize starch b at a concentration of about 29.53% w/w, sodium starch glycolate at a concentration of about 5.06% w/w, cross-linked polyvinylpyrrolidone (Crospovidone XL 10) at a concentration of about 6.57% w/w, and perfume at a concentration of about 0.54% w/w.

or said composition comprises:
a combination of cocamidopropyl betaine, sodium cocoyl taurate and capryl glucoside at a concentration of about 36.667% w/w, a combination of ethylhexylglycerin, propylene glycol and octenidine HCl at a concentration of about 0.067% w/w, xylityl glucoside at a concentration of about 2.583% w/w, decyl polyglucoside at a concentration of about 3.333% w/w, sodium cocoyl apple at a concentration of about 3.333% w/w, maize starch b at a concentration of about 33.950% w/w, sodium starch glycolate at a concentration of about 8.333% w/w, cross-linked polyvinylpyrrolidone (Crospovidone XL 10) at a concentration of about 10.833% w/w, and perfume at a concentration of about 0.900% w/w or said composition comprises:
magnesium aluminometasilicate at a concentration of about 16% w/w, cocamidopropyl betaine at a concentration of about 5% w/w, sodium methyl cocoyl taurate at a concentration of about 9% w/w, sodium cocoyl isethionate at a concentration of about 8% w/w, a combination of ethylhexylglycerin, propylene glycol and octenidine HCl at a concentration of about 1% w/w, xylityl glucoside at a concentration of about 3. % w/w, decyl polyglucoside at a concentration of about 3% w/w, sodium cocoyl apple at a concentration of about 3% w/w, maize starch b at a concentration of about 34% w/w, sodium starch glycolate at a concentration of about 9% w/w, cross-linked polyvinylpyrrolidone (Crospovidone XL 10) at a concentration of about 7% w/w, and perfume at a concentration of about 1% w/w.

10) The saponification free cleansing composition of any of the above embodiments, wherein the composition is a pharmaceutical or cosmeceutical composition;
wherein said composition is in a form selected from solid, liquid, foam, aerosol, or any combinations thereof;
and wherein the solid composition is formulated in a form selected from a group comprising tablet, capsule, pellet, spray dried material of various particle size distributions, powder, granule, and bar; wherein the bars which can be packed as blisters, strips, sachets, sprayers, dispensers, press/tap/slide-to-open containers, wraps and combinations thereof.

11) The saponification free cleansing composition of any of the above embodiments, wherein the composition is in the form of granule, said granule obtained by passing through a mesh size of 14 to 80;
wherein the composition comprises 0.25 to 25% w/w moisture to formulate the composition in solid form;
and wherein the composition comprises more than 25% w/w moisture to formulate the composition in liquid, foam or aerosol form.

12) A process for preparing the saponification free cleansing composition as defined in any of the above embodiments, said composition comprising cleansing agent, adsorbing agent and excipient,
the process comprising mixing the cleansing agent, the adsorbing agent and the excipient to obtain the saponification free cleansing composition.

13) A process for preparing the saponification free cleansing composition as defined in any of the above embodiments, said process comprising:
mixing surfactant, moisturizing agent, solvent, skincare agent, deodorizing agent, chelating agent, foaming agent and perfuming agent to obtain a Mixture 1;
blending the Mixture 1 with an adsorbing agent to obtain Mixture 2 followed by passing the Mixture 2 through mesh to obtain Mixture 3,
mixing the Mixture 3 and a filler to obtain Mixture 4; and
mixing the Mixture 4 with a disintegrant or super disintegrant to obtain the saponification free cleansing composition.

14) A process for preparing the saponification free cleansing composition as defined in any of the above embodiments, said process comprising:
mixing surfactant, moisturizing agent, solvent, skincare agent, chelating agent, deodorizing agent and foaming agent and perfuming agent to obtain a Mixture 1a;
spray drying the Mixture 1a to obtain spray dried powder/granules;
mixing the spray dried powder/granules and a filler to obtain Mixture 2a; and
mixing the Mixture 2a with a disintegrant or super disintegrant to obtain the saponification free cleansing composition.

15) A process for preparing the saponification free cleansing composition as defined in any of the above embodiments, said process comprising mixing surfactant, moisturizing agent, solvent, skincare agent, deodorizing agent, foaming agent, disintegrant or super disintegrant, and filler to obtain saponification free cleansing composition.

16) Use of the saponification free cleansing composition of any of the above embodiments for application in personal hygiene, cleansing or sanitizing skin, cleansing or sanitizing inanimate objects/surfaces, paediatric application, geriatric or veterinary application, washing of utensils or clothes, cleansing stationary articles, getting rid of sticky material(s) from surfaces, potentiation of routinely used detergents, or any combination of applications thereof.

The invention claimed is:

1. A saponification free cleansing composition consisting of 100% by weight of the following:
magnesium aluminometasilicate at a concentration of about 22.68% w/w, cocamidopropyl betaine at a concentration of about 11.07% w/w, sodium methyl cocoyl taurate at a concentration of about 6.92% w/w, sodium lauryl sulphate at a concentration of about 6.92% w/w, alkane sulfonate at a concentration of about 1.38% w/w, octenidine HCl at a concentration of about 1.14% w/w, xylityl glucoside at a concentration of about 1.66% w/w, starch at a concentration of about 20.75% w/w, microcrystalline cellulose at a concentration of about 20.75% w/w, sodium starch glycolate at a concentration of about 4.15% w/w, cross-linked polyvinylpyrrolidone at a concentration of about 2.77% w/w, colloidal silicon dioxide at a concentration of about 0.55% w/w, and a perfuming agent at a concentration of about 0.28% w/w.

2. A saponification free cleansing composition consisting of 100% by weight of the following:
magnesium aluminometasilicate at a concentration of about 10.15% w/w, cocamidopropyl betaine at a concentration of about 12.19% w/w, sodium methyl cocoyl taurate at a concentration of about 10.15% w/w, sodium lauryl sulphate at a concentration of about 6.09% w/w, alkane sulfonate at a concentration of about 2.03% w/w, sodium cocoyl isethionate at a concentration of about 10.15% w/w, starch at a concentration of about 14.22% w/w, microcrystalline cellulose at a concentration of about 23.15% w/w, sodium starch glycolate at a concentration of about 6.09% w/w, cross-linked polyvinylpyrrolidone at a concentration of about 4.06% w/w, pyrrolidone carboxylic acid at a concentration of about 0.41% w/w, colloidal silicon dioxide at a concentration of about 0.81% w/w, sorbic acid at a concentration of about 0.08% w/w, and a perfuming agent at a concentration of about 0.41% w/w.

3. A saponification free cleansing composition consisting of:
sodium cocoyl taurate at a concentration of 11.31% w/w, sodium lauryl sulphate at a concentration of 6.79% w/w, sodium cocoyl isethionate at a concentration of 13.57% w/w, starch at a concentration at a concentration of 15.84% w/w, microcrystalline Cellulose at a concentration of 27.15% w/w, lactose at a concentration at a concentration of 9.05% w/w, sodium starch Glycolate at a concentration of 6.79% w/w, cross-linked polyvinylpyrrolidone at a concentration of 4.52% w/w, pyrrolidone Carboxylic Acid at a concentration of 0.45% w/w, colloidal silicon dioxide at a concentration of 3.17% w/w, Sorbic acid at a concentration of 0.09% w/w, a perfuming agent at a concentration of 1.27% w/w.

* * * * *